United States Patent [19]

Klett

[11] Patent Number: 4,900,857

[45] Date of Patent: Feb. 13, 1990

[54] PHOSPHORUS-CONTAINING ORGANO SILANES

[75] Inventor: Michael W. Klett, Allison Park, Pa.

[73] Assignee: PPG Industries, Inc., Pittsburgh, Pa.

[21] Appl. No.: 188,234

[22] Filed: Apr. 29, 1988

Related U.S. Application Data

[63] Continuation-in-part of Ser. No. 31,629, Mar. 30, 1987, abandoned.

[51] Int. Cl.$^4$ ............................................... C07F 7/18
[52] U.S. Cl. ..................................................... 556/405
[58] Field of Search ......................................... 556/405

[56] References Cited

U.S. PATENT DOCUMENTS

| | | | |
|---|---|---|---|
| 2,889,349 | 6/1959 | Garden et al. | 556/405 |
| 2,978,471 | 4/1961 | Fekete | 556/405 |
| 2,996,530 | 8/1961 | Fekete | 556/405 |
| 3,067,229 | 12/1962 | Fekete | 556/405 |
| 3,197,431 | 7/1965 | Lanham et al. | 556/405 X |
| 3,202,633 | 8/1965 | Fekete | 556/405 X |
| 3,203,925 | 8/1965 | Fekete | 556/405 X |
| 3,869,390 | 3/1975 | Kotzsch et al. | 556/405 X |
| 4,093,641 | 6/1978 | Plueddemann | 556/405 |

*Primary Examiner*—Paul F. Shaver
*Attorney, Agent, or Firm*—Kenneth J. Stachel

[57] ABSTRACT

New phosphorus-containing organo functional silane are produced through reactions such as condensation or Michael's addition reactions of hydroxyl-containing and/or methylol-containing phosphorus compounds and organo-functional silanes having at least one active hydrogen associated with a nitrogen in the organo moiety or an isocyanato, anhydride, alkene or epoxy moiety. The reaction can be conducted at a temperature in the range of around less than ambient to around 150° C. with or without a solvent in a molar ratio of around 1:1 to around 1:4 of the phosphorus-containing compound to the silane.

13 Claims, 3 Drawing Sheets

PHOSPHORUS-CONTAINING ORGANO SILANES

This application is a continuation-in-part application of application Ser. No. 31,629, filed Mar. 30, 1987.

The present invention is directed to producing phosphorus-containing organo silane compounds.

Generally, currently available organo silane compounds having phosphorus are produced by more vigorous, severe, or complex reaction conditions like Grignard reactions and catalyzed free radical reactions usually in the presence of an organic solvent. Also many of these silane compounds have limited hydrolytic stability.

For instance, U.S. Pat. No. 3,122,581 (Pike) teaches the reaction of a phosphorus compound and a silicon compound. The phosphorus compound has one trivalent or pentavalent phosphorus atom with at least one hydrogen bonded to the phosphorus. The silicon compound has at least one silicon atom and at least one ethylenically unsaturated aliphatic or alicyclic hydrocarbon radical attached to the silicon. The process is preferably conducted under the influence of a catalyst which encourages the addition of the phosphorus compound to the double bond of the ethylenically unsaturated aliphatic or alicyclic hydrocarbon of the silicon compound to produce monomeric and/or polymeric products. The temperature of the reaction is from around 50° C. to 250° C. depending upon the rate of decomposition of the particular free radical catalyst. Although the reaction could be conducted without a solvent, a solvent can be employed and when employed, should be selected so that it is non-reactive toward the reactants and the catalyst. Suitable solvents include: benzene, toluene, and the like.

U.S. Pat. No. 3,869,340 (Kotzsch et al.) shows an organo silane with a phosphate ester as an adhesive produced by a process similar to that of U.S. Pat. No. 3,122,581. The product compounds have the general formula:

wherein each R is independently a substituted or unsubstituted aliphatic radical, each A is a bivalent alkylene or arylene radical or a bivalent oxyalkylene or oxyarylene radical joined by its oxygen to the phosphorous atom, and m, n, p, and x are each values of 0 or 1, B is either a bivalent oxygen radical, an —NH— radical, an —NR— radical or an —S— radical when p is equal to 1 and y is equal to 1 to 20.

British patent specification No. 1,179,242 (Owen et al.), where the applicant was Midland Silicones Limited, teches the production of organo silicon compounds having the general formula:

Each R is a monovalent hydrocarbon radical or a monovalent radical composed of hydrogen, carbon and oxygen atoms. Each R' is a monovalent hydrocarbon radical containing at least two carbon atoms or a monovalent radical composed of carbon, hydrogen and oxygen. Other variables in the formula include: x as a hydrogen atom or a monovalent hydrocarbon radical; y as a monovalent hydrocarbon radical; k as 0 or 1; a as 0, 1 or 2; b as 0, or 1; and the sum of a+b as 0 or an integer from 1 to 3. These compounds are characterized by their methylene linkage between the phosphorus and silicon atoms. Preparation of these compounds may be achieved for example, by reacting the appropriate chlorophosphine compound with a silicon Gringard compound containing the grouping SiCH$_2$MgCl. Another method of producing these compounds is by reacting an alkali metal derivative of a phosphine of the general formula MP(x) (y). In this formula, the M represents an alkali metal, preferably sodium, with an organo silane. The organo silane has the general formula: R$_a$R'$_b$Si[CH$_2$Hal]4-a-b, wherein Hal represents a halogen atom, preferably chlorine and R or R' are the same types of compounds as the R and R' for the phosphorus. The reaction of the alkali metal phosphino compound and the silane according to this latter process is best carried out in the presence of a polar solvent such as liquid ammonia.

Russian Patent Specification No. SU-418458 O. E. Peregud et al. published 3/5/74 discloses without specifying a method of preparation a phospho-organosilicon amine compound having the formula:

This compound is coated onto glass fibers at either the lubrication or sizing stage. The treated fibers are used to reinforce polymers.

The aforementioned reactions are generally fairly complex involving elevated temperatures or organic solvents, or Gringard reactions or the like. Also the phosphate ester-containing compounds have hydrolytic instability, which may limit their use in humid environments. It would be beneficial to the art to have more stable phosphorus containing organo silane compounds produced in a more fascile manner and at less severe conditions and preferably in an aqueous environment or in an aqueous soluble form.

SUMMARY OF THE INVENTION

The present invention is phosphorus-containing organo silanes produced by more fascile reactions under generally mild conditions. The reactants are methylol-containing or hydroxyl-containing trivalent, quaternary or pentavalent phosphorus compounds and organo functional silane, where the organo moiety has at least one active hydrogen. The silane is selected from nitrogen-containing silanes like isocyanato organo functional silanes, ureido organo functional silanes and amino-functional organo silanes, epoxy-organo functional silanes like gamma-glycidoxyalkyl trialkoxy silane, unsaturated organo functional silane, or anhydride-containing organo functional silane. The reaction can be conducted in a range from subambient to elevated temperatures and pressures and with a rate of reaction to favor the production of the phosphorus-containing organo silane over formation of any dimer or polymer species of a hydrolyzed silane. The reaction occurs with or without a catalyst. The phosphorus-containing organo silanes have the general formula:

$$(R'OR)_{4-(a+b+c)} - \overset{\overset{\displaystyle Wa}{|}}{\underset{\underset{\displaystyle Yc}{|}}{P}} - R - X_b \qquad \text{(Formula I)}$$

In this formula, W is oxygen, or sulfur double bonded to the phosphrous or an (R'OR) moiety or a lone pair of electrons and a is an integer of zero or 1. The Y of the formula is hydrogen, alkyl, aryl, hydroxy or the (R'OR) moiety, and c is an integer of 0 to 2. In Formula I, X is a moiety of an organo functional alkoxy silane or hydrolysis derivative thereof and where:

R' is hydrogen, or substituted or unsubstituted aliphatic radicals or mixture thereof; and R is a bivalent substituted or unsubstituted alkylene or arylene radial; and a, b, and c are integers where b is 1 to 4, a is 0 or 1, c is 0–2, and when c is at least 1 and a is zero and b is 1 or 2, the compound can be in salt form as the cation with anions selected from the group consisting of halides, sulfates, formates, acetates and phosphates.

Generally, the method of producing the phosphorus-containing organo silanes of the present invention is by condensation reaction. Although a Michael's addition reaction is used when one of the reactants is an organo silane containing unsaturation. In the condensation reactions, the reactants contact each other with or without the presence of a solvent at conditions of temperature in a range from ambient to elevated (around less than 150° C. (302° F.)) and at pressures of subatmospheric to superatmospheric and at mole ratios of around 1:1 to around 1:4 of the phosphorus-containing reactant to the silane-containing reactant. These conditions are varied to suit the rate of reaction for the various reactants.

DETAILED DESCRIPTION OF THE INVENTION

In preparing the phosphorus-containing organo silane compound various phosphorus-containing compounds can be used as reactants. Nonexclusive examples of the phosphorus-containing compounds include: methylolphosphorus compounds like tetrakis (hydroxy methyl) phosphonium salts, for example, the formate, acetate, phosphate, sulfate or halides like bromide and chloride; and tris (hydroxymethyl) phosphine oxide, hereinafter referred to as "THPC" and "THPO", respectively, and tetrakis (hydroxymethyl) phosphonium hydroxide; and phosphines like trishydroxy methylphosphine, bishydroxy methyl methylphosphine, and other trifunctional alkyl phosphines. The compounds with the phosphorus linked (R'OR) group like a methylol group are produced by reacting the THPC or THPO or phosphines or mixtures thereof with at least one other compound to form a product, that contains at least one P R'OR group.

The organo functional silane reactant is a nitrogen-containing organo silane, organo functional silane having active hydrogens associated with the nitrogen and also having a carbon atom double bonded to an oxygen like gamma ureido alkyl alkoxy silane or is an isocyanato-containing alkyl trialkoxy silane or is an epoxy-containing alkyl trialkoxy silane or anhydride-containing organo functional silane or an organo functional silane with unsaturation in the organic moiety or an organo silane with a haloalkyl or haloaryl moiety. The former silane is available from Union Carbide Corporation under the trade designation A-1160 and isocyanato-containing silane is available from Union Carbide Corporation under the trade designation Y-9030, and the latter silanes can be gamma-glycidoxypropyltrimethoxy silane like that from Union Carbide Corporation under the trade designation A-187 silane or beta-(3,4-epoxy cyclohexyl) ethyl trimethoxysilane. The ureidopropyl trialkoxysilane as A-1160 is a 50 percent mixture with methanol and has: formula weight of 264.1 gm, flash point of 43 (ASTM-D-56), specific gravity at 25/25° C. of 0.988 and a refractive index at 25° C. of 1.386. This silane as well as the epoxy silane is useable in unhydrolyzed form and/or hydrolyzed form. The isocyanate-containing organo silane should be used in its unhydrolyzed form. The methacryloxypropyl trimethoxy silane is an example of an unsaturated organo silane, and is available from Union Carbide Corporation under the trade designation A-174 silane. An example of a haloalkyl-containing organo silane is 3-bromopropyl triethoxysilane available from Dynamit Nobel under the trade designation of B2620. The anhydride-containing silane has a formula of:

Formula II and is available from Wacker-Chemie GmbH under the trade designation Wacker Silane GF-20.

The reactants are combined in a suitable reaction vessel that can withstand the conditions of the condensation or Michael's addition reaction and which is well known to those skilled in the art. The temperature of the reaction is preferably from ambient temperature up to around 80° C., but the temperature can range from a subambient to preferably not above 100° C. These temperatures are conventional for conducting condensation reactions. The pressure for the reaction is preferably at ambient pressure, although subambient and superatmospheric pressures can be used; however, it is preferred for convenience, that the process be carried out at atmospheric pressure. If one or more of the reactants is too volatile for practical reaction at atmospheric pressure, the reaction can conveniently be run at superatmospheric pressure in a pressure vessel. When a phosphine and/or isocyanate-containing silane are the reactants, it is preferred that the reaction be carried out in an inert atmosphere such as in argon or nitrogen to prevent oxidation of the phosphine by atmospheric oxygen or reaction of the isocyanate with water. A contacting of the reactants occurs either simultaneously or sequentially to allow for dissolution of a reactant and the other reactants or in a solvent as is known to those skilled in the art of chemical reactions. The molar ratio of the reactants can range from 1:1 to 1:4 of the phosphorus compound to the organo functional silane. This allows for the reaction product having multiple silane groups, around 1 phosphorus atom. Preferably the molar ratio in the range of around 1 to around 1.

A solvent is not necessary for reactants in a liquid phase where they can be reacted in a neat reaction. A solvent can be used whether the reactants are in a liquid or solid phase where the solvent for the solid phase reactants is selected to dissolve the solids. Any aprotic solvent can be used, and an aprotic solvent is desirable when the reactant is the isocyanto organo functional silane. The most preferred solvent for use with the phosphine type reactant and the isocyanto-containing silane is the trialkyl phosphates like triethyl phosphate.

Additional conditions for the reaction include the use of a basic catalyst which has a limited basicity. The basic catalyst should not be so strong as to abstract a hydrogen from the hydroxy methyl (methylol) group of the phosphorus-containing compound as in tetrakis hydroxymethyl phosphonium sulfate. This would cause a formation of formaldehyde. The function of the basic catalyst in the reaction is to both control the pH and to accelerate the condensation reaction in a controlled manner.

An effective pH is preferably maintained in the condensation reaction to avoid formation of free formaldehyde. This effective pH control allows for the production of methylene bridges between the carbon of the phosphonium compound and the nitrogen containing compound. Preferably the pH is controlled within the range of about 5 to about 7. Effective pH control is provided by the presence of an effective amount of a tertiary amine like trialkanol amines; for example, triethanolamine, diethanolamine, ethanolamine, and triethyl amine or alkanol amines and alkanyl amines, such as ethanol amine, dimethyl amino ethanol, diethyl amino ethanol, diisopropanol amine, triisopropanolamine, 4-hydroxy-n-butyl amine, 2-dimethyl amino, 2-methyl propanol and the like having a formula $R_2'N\text{-}CH_2\text{-}CH_2\text{-}OH$ wherein 1 R' is methyl or ethyl and the other independently is ethyl or 2 hydroxy ethyl; an ammonium salt catalyst such as diammonium phosphate, ammonium chloride, ammonium carbonate and ammonium hydroxide. Other suitable catalysts include: organic amines, amides, and imines such as pyridine, acrylamide and polyethyleneimine. The function of the catalyst is to accelerate the condensation reaction in a controlled manner, but the catalyst may also react with the phosphonium salt. In the order of decreasing preference, those specific alkanolamines which are more highly preferred are triethanolamine, diethanolamine, ethanolamine, N-methyl ethanolamine and N-N-dimethyl ethanolamine and the like. The time of the reaction depends upon the temperature of the reaction and can range from several days for ambient temperature reactions to around 10 minutes for higher temperature reactions. Because the reaction is limited to control the formation of methylene bridges between the monomers and to avoid abstraction of hydrogen to keep intact as many hydroxyl groups as possible, any water of the condensation reaction need not be removed.

The reaction product has the general structure of Formula I.

where W, X, Y, R, R', a, b and c have the same meaning as for the aforementioned Formula I, and where the (R'OR), W, R-X and Y groups may have interchangeable positions about the phosphorus, P. Nonexclusive examples of moieties for X in Formula I include:

where:

R° is a hydroxyl group, and

R' is an alkyl group having 1 to 5 carbon atoms or a mixture thereof between the three groups joined at the silicon; and q is an integer of 1 to 6, preferably 1 to 3 and p is an integer of 1 to 3.

In Formula I, where the $X_b$ moiety is Formula A, the reactants are tetrakishydroxy phosphonium compounds and ureido propyl trialkoxy silane. Where the $X_b$ moiety is Formula B, the reactants are tetrakis hydroxymethyl phosphonium compound and gamma isocyanato propyltrialkoxy silane. With Formula C as the $X_b$ moiety, the reactants are a glycidoxypropyltrialkoxy silane and either tetrakis hydroxy phosphonium compound or tetrakis hydroxy methyl phosphonium compound, respectively. When the $X_b$ moiety is Formula D, the reactants are the anhydride-containing organo silane and the tetrakis hydroxymethyl phosphonium compound. With Formula E as the $X_b$ moiety, the reactants are the methacryloxyalkyl alkoxysilane and tetrakis hydroxymethyl phosphonium compound.

Generally for a condensation reaction, the —R—$X_b$ moiety has the formula:

In Formula II, x is an integer of 0 or 1 and when 1 then A is either of two types of compounds. One is a bivalent alkylene or arylene radical when y 32 1 and B is a bivalent —NH' or —NR— radical. The second is a bivalent oxygen, SULFUR oxyalkylene or oxyarylene radical when y=0 or y=1 and B is a bivalent alkylene or arylene radical. The oxygen of these radicals can be joined to a carbon of D when D is a carbonyl group or to a carbon of B when B is present as a bivalent alkylene or arylene radical. Alternatively, the oxygen of these radicals can be joined to the phosphorus when D is a —CH—OH group and y=0.

Also in Formula II, y is an integer of 0 or 1, and when 1, B is selected from two types of compounds. The B in the Formula II can be a bivalent (N—H)— or —(N—R)— radical, when x=1 and A is a bivalent alkylene radical. Alternatively, B can be a bivalent alkylene or oxyalkylene and D is a —(CH—OH)— radical.

Also in Formula II, D is a bivalent carbonyl or —CH—OH radical.

Also in Formula II, the R and R' can independently be substituted or unsubstituted aliphatic radicals or mixtures thereof and R° is a hydroxyl group or can also be a hydrogen independently or in mixture with the (OR) group, around the Si group. The p for the R° moiety off of the Si group is an integer from 0 to 3.

All of the reaction products having the various formulas can be produced under the aforementioned similar condensation reaction conditions, except for Formula G, which is produced by the Michael's addition reaction.

It is believed, but the present invention is not limited by this belief, that the structure of the reaction product is tetrahedral with a Wa moiety of Formula I forming the apex of the tetrahedral and the moieties (R' OR) and Yc and X$_b$ forming the base with the phosphorus in the center of the tetrahedral structure. The reaction products are usually in the liquid phase or an oil-like product or can be salts that are soluble in water.

Any unreacted components can be separated from the reactant product by methods known to those skilled in the art, but generally the reaction is near completion so that separation of unreacted components from the reaction product is not necessary.

The present invention is further elucidated without limiting the generality or scope thereof in the following preferred embodiment and examples.

PREFERRED EMBODIMENT

Figure 1:
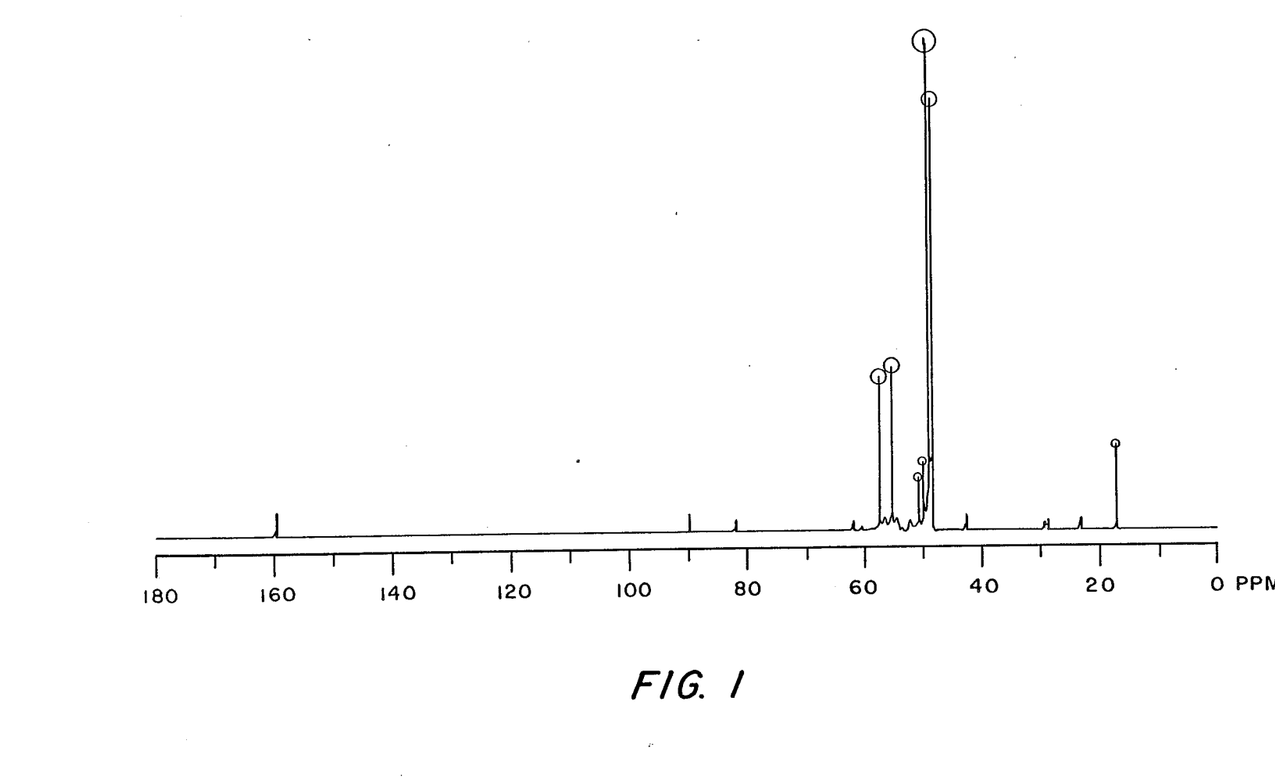
FIG. 1 is a nuclear magnetic resonance curve of the reaction product of a ureido functional organo silane and tetrakis hydroxymethyl phosphonium sulfate where dioxane was used as a shift reference.

To a stirring solution of ten grams (18.5 millimoles (mmoles) of tetrakis hydroxymethyl phosphonium sulfate (Pyroset TKOW or Retardol S) in 20 grams of water, there was added 1 gram (6.7 mmoles) of triethanolamine and diammonium phosphate in an amount of 0.1 gram (0.76 mmoles). To this mixture there was slowly added 5 grams (9.5 mmoles) of gamma ureido propyltriethoxy silane with 24 hours of additional stirring. The ratio of the reactants is a 1:1 molar ratio and the temperature of the reaction is ambient temperature to about 40° C. An NMR analysis (13C) was performed in an art recognized manner and the spectrum is shown in FIG. 1. As shown, the signals at 50.81 and 50.16 ppm indicate formation of a urea-tetrakishydroxymethylphosphonium sulfate condensate.

EXAMPLE 1

To a stirring solution of trihydroxymethylphosphine (2.0 gm, 0.16 mmoles) in 8 gm. of triethylphosphate there was added 2 drops of triethylamine. The mixture was warmed to 40°–60° C. under a nitrogen atmosphere and isocyanato-propyltriethoxylsilane as Y-9030 (3.98 gm., 0.16 mmoles) was slowly added. A temperature of 40°–60° C. was maintained until complete disappearance of the isocyanate band at 2264 cm$^{-1}$ as ascertained by infrared spectroscopy. The new silane coupling agent displays the characteristic urethane absorption at 1730 cm$^{-1}$ noted in FIG. 2.

Figure 2:
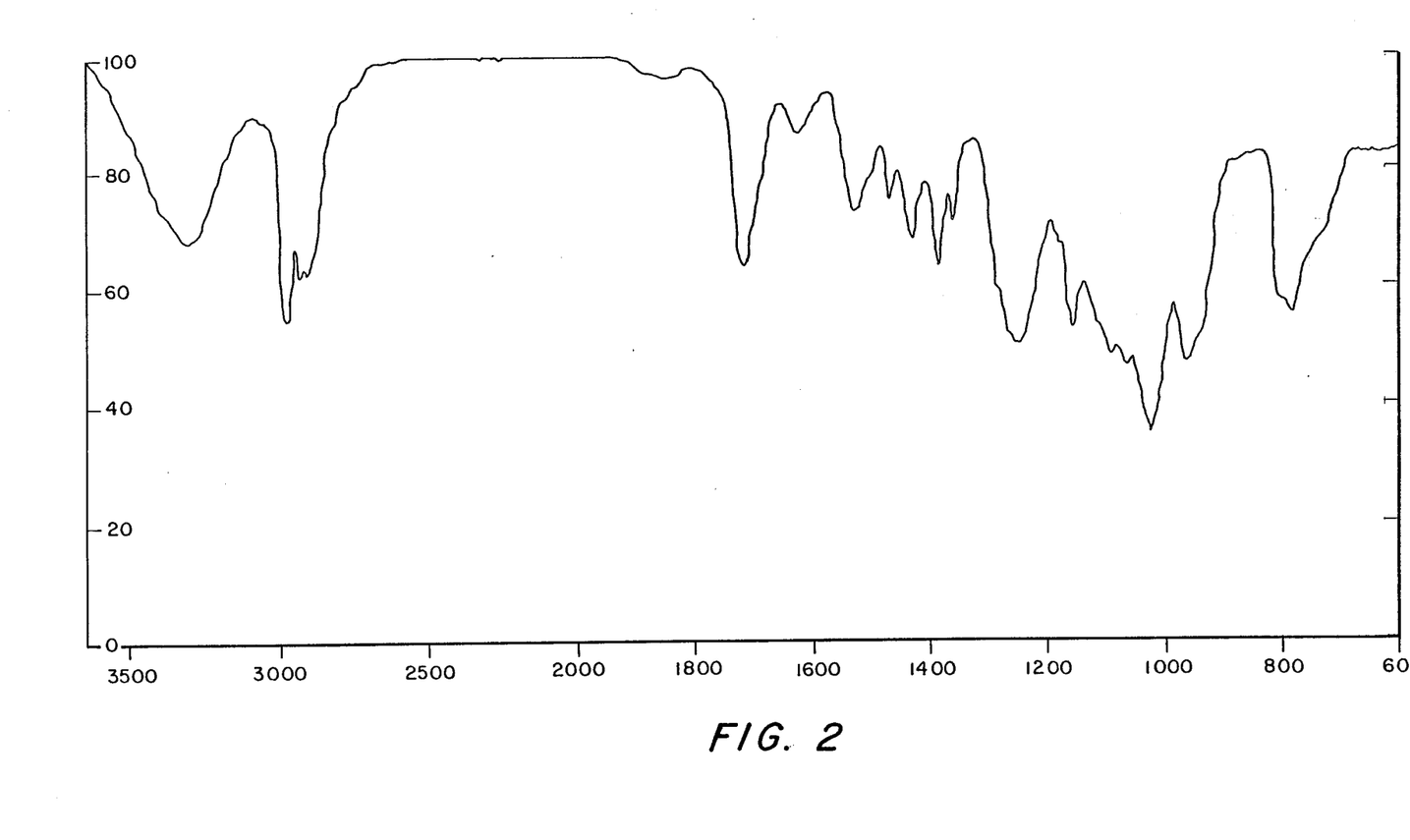
FIG. 2 is an infrared spectra of the phosphorus-containing organo silane produced according to Example 1.
Figure 3:
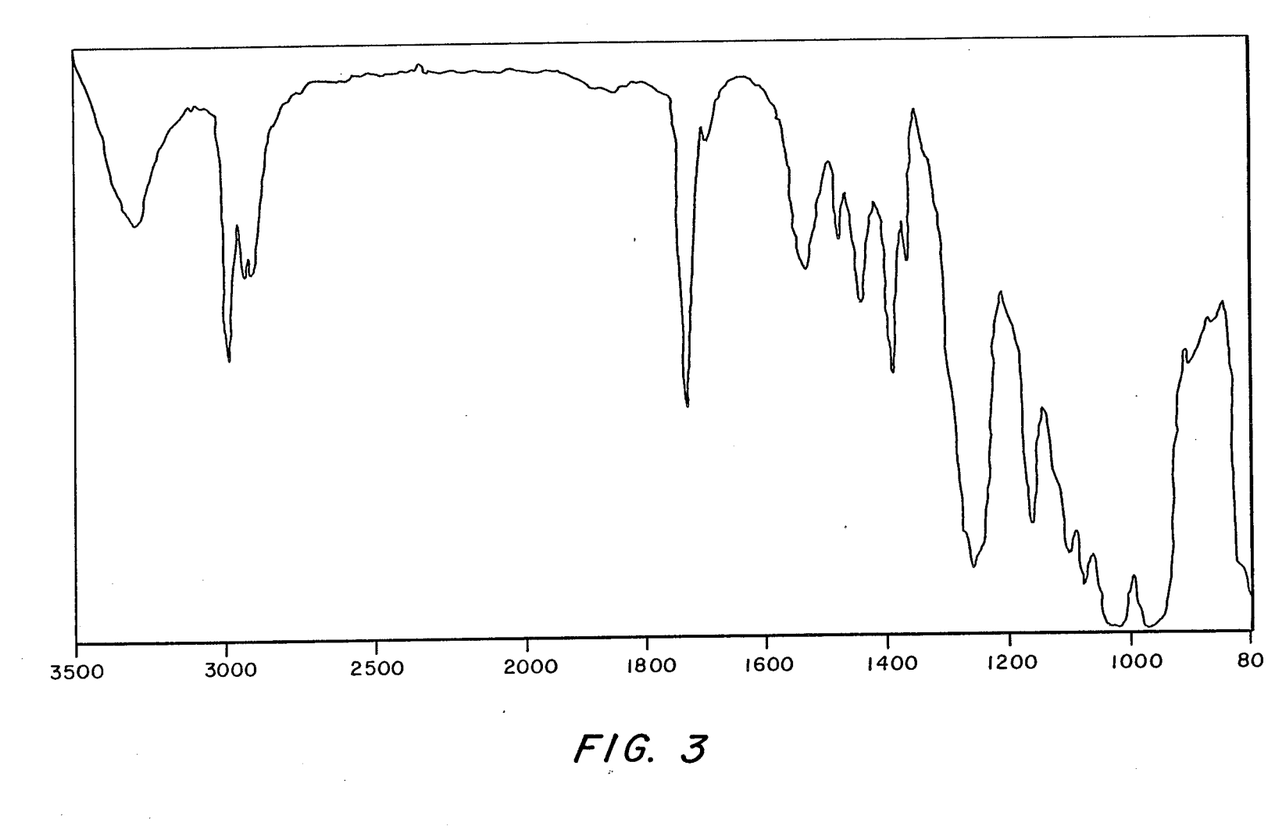
FIG. 3 is an infrared spectra of the phosphorus-containing organo silane produced according to Example 2.

The spectra was made as was that of FIG. 3 from smeared film on a Perkin-Elmer model 1700. The plot parameters were an abscissa expansion of 1 and an ordinate scale of 1, the plot range was 4000 to 600 and the ordinate offset was 0.

EXAMPLE 2

To a stirring solution of trishydroxymethylphosphine oxide (2.0 gm., 0.14 mmoles) in 10 gm. of triethylphosphate there was added 2 drops of triethylamine. The mixture was warmed to 60°–80° C. under a nitrogen atmosphere isocyanato-propyltriethoxysilane as Y-9030 (3.6 gm., 0.14 mmoles) was slowly added. A temperature of 60°–80° C. was maintained until complete disappearance of the isocyanate band at 2264 cm$^{-1}$ as ascertained by infrared spectroscopy. The new silane coupling agent displays the characteristic urethane absorption at 1732 cm$^{-1}$ noted in FIG. 3.

The phosphorus containing organo silanes of the present invention are useful in treating glass substrates as adhesion promoters and for increasing the softening point of the glass. Also these materials would be useful in coating other inorganic or metallic oxide surfaces such as inorganic oxide films, particulate fillers and pigments and fibers such as steel fibers, aluminum, and glass fibers. Aluminum and steel fibers are considered inorganic oxide surfaces because they have a surface layer which is oxidized although their subsurfaces are not. The phosphorus containing organo silane treatment usually involves coating the surface with the hydrolyzate of the phosphorus organo functional hydrolyzable silane. In this fashion, the silanes act as adhesion promoters of the inorganic oxide surfaces with various polymeric matrices such as polyesters, polyurethanes, epoxies, nylons and other polymers.

I claim:

1. Phosphorus-containing-organo-silane compound of the general formula:

$4 - (a + b + c)$

I W is oxygen, sulfur, (R'OR) or a lone pair of electrons, where the
oxygen and sulfur are double bonded to the phosphorus, and where
a is an integer of 0 or 1;

II Y is a hydrogen, alkyl, aryl, hydroxy or an (ROR') group, and where
c is an integer 0 or 1; and III X is trialkoxy organo functional silane moiety or hydrolysis derivative thereof and where:
R' is hydrogen, or substituted or unsubstituted aliphatic radicals or mixtures thereof; and
R is a bivalent substituted or unsubstituted alkylene or arylene radical; and
a, b, c are integers where b is 1 to 4, a is 0 or 1, c is 0–2, and when C is at least 1 and a is zero and b is 1 or 2, the compound can be in salt form as the cation with anions selected from the group consisting of halides, sulfates, formates, acetates and phosphates.

2. Compound of claim 1, wherein X has the general formula:

$$[A_x-B_y-D-R'-Si(OR)_{3-p}]$$
$$R^o_p$$

where:
(i) x is an integer of 0 or 1 and when 1
A is: (1) a bivalent alkylene or arylene radical when y=1 and B is a bivalent —NH— or —NR— radical, or
(2) is a bivalent oxygen oxyalkylene or oxyarylene radical when y=0, where the oxygen is joined to a carbon of D when D is a carbonyl group or where the oxygen is joined to phosphorus when D is a —CH—OH group, or when y=1 and B is a bivalent alkylene or arylene, radical where the oxygen is joined to the carbon of B;
(ii) y is an integer of 0 or 1 and when 1
B is (1) a bivalent -NH- or -NR- radical when x=1 and A is a bivalent alkylene or arylene radical, or
(2) a bivalent alkylene or arylene radical when x=1 and A is a bivalent oxyalkylene or oxyarylene and D is a —CH—OH radical;

$$-\left(\begin{array}{c}O\\\|\\C\end{array}\right)-$$

(iii) D is a bivalent carbonyl or —CHOH radical;
(iv) R° is a hydroxyl group or hydrogen group and p is an integer from 0 to 3;
(v) R is hydrogen, or substituted or unsubstituted aliphatic radicals or mixture thereof;
(vi) R' is a bivalent substituted or unsubstituted alkylene or arylene radical.

3. The compound of claim 1 having the IR spectra of FIG. 2.

4. The compound of claim 1, having the NMR spectra of FIG. 1.

5. The compound of claim 1 that is:

$$(HOR)_{[3-(a+b)]}\overset{W_a}{\underset{Y_c}{P}}-R-NH-\overset{O}{\overset{\|}{C}}-NH-(CH_2)_3-Si-(OR')_3 \quad (I_5)$$

wherein:
R' is hydrogen or alkyl group having 1 to 3 carbon atoms or a mixture thereof between the three groups joined to the silicon;
R is a methylene group and
a and c are integers of 1 or zero; and where a and c are both zero the compound is a salt with compound ($I_5$) being the cation and the anion is selected from the group consisting of halides, sulfates, formates, acetates and phosphates.

6. The compound of claim 1 that is:

$$(HO-R)_{\overline{3-(a+c)}}\overset{W_a}{\underset{Y_c}{P}}-CH_2O-\overset{O}{\overset{\|}{C}}-NH-(CH_2)_3-Si(OR')_3 \quad (I_6)$$

wherein:
R' is hydrogen or alkyl group having 1 to 3 carbon atoms or a mixture thereof between the three groups joined to the silicon;
R is a methylene group and
a and c are integers of 1 or zero; and where a and c are both zero the compound is a salt with compound $I_6$ being the cation and the anion is selected from the group consisting of halides, sulfates, formates, acetates and phosphates.

7. The compound of claim 1 that is:

$$(HO-R)_{\overline{3-(a+c)}}\overset{W_a}{\underset{Y_c}{P}}-CH_2-O-CH_2-\overset{OH}{\overset{|}{C}H}-(CH_2)_3Si(OR')_{3-p}\overset{R^o_p}{|} \quad (I_7)$$

wherein:
R' is hydrogen or alkyl group having 1 to 3 carbon atoms or a mixture thereof between the three groups joined to the silicon;
R is a methylene group;
R° is a hydroxyl group or a hydrogen;
a, c and p are integers where a and c are of 1 or zero; and where a and c are both zero the compound is a salt with compound $I_7$ being the cation and the anion is selected from the group consisting of halides, sulfates, formates, acetates and phosphates and where p has a value from 1 to 3.

8. The compound of claim 1 that is:

$$(HO-R)_{\overline{3-(a+c)}}\overset{W_a}{\underset{Y_c}{P}}-CH_2-O-\overset{O}{\overset{\|}{C}}-CH_2-\overset{}{\underset{CO_2H}{C}H}(CH_2)_3Si(OR')_{3-p}\overset{R^o_p}{|} \quad (I_8)$$

wherein:
R' is hydrogen or alkyl group having 1 to 3 carbon atoms or a mixture theeof between the three groups joined to the silicon;
R is a methylene group;
R° is a hydroxyl group or hydrogen; and
a, c and p are integers where a and c have values of 1 or zero; and where when a and c are both zero, the compound is a salt with compound ($I_8$) being the cation and the anion is selected from the group consisting of halides, sulfates, formates, acetates and phosphates, and where p has a value from 1 to 3.

9. The compound of claim 1 that is:

$$(HO-R)_{\overline{3-(a+c)}}\overset{W_a}{\underset{Y_c}{P}}-CH_2-O(CH_2)_2\overset{O}{\overset{\|}{C}}-O(CH_2)_3Si-(OR')_{3-p}\overset{R^o_p}{|} \quad (I_9)$$

wherein:
- R' is hydrogen or alkyl group having 1 to 3 carbon atoms or a mixture thereof between the three groups joined to the silicon:
- R is a methylene group;
- a, c and p are integers where a and c have values of 1 or zero; and where when a and c are both zero, the compound is a salt with compound ($I_9$) being the cation and the anion is selected from the group consisting of halides, sulfates, formates, acetates and phosphates, and where p has a value of 1 to 3.

10. The compound of claim 1, wherein X is selected from the group consisting of:

11. A method of producing phosphorus-containing organo silanes, comprising:
contacting methylol-containing phosphorus compounds with organo functional silanes, selected from the group consisting of nitrogen-containing organo silanes having at least one active hydrogen associated with the nitrogen wherein the organo moiety also has a carbonyl group and isocyanato-containing organo silanes, and glycidoxy-containing organo silanes in the presence of a basic catalyst in the presence of a phosphorus-containing solvent in a molar ratio of 1:1 at a temperature in the range of around 60° to 80° C. (140° F.–176° F.) for a sufficient period of time to enable condensation reaction between the reactants,
separating the phosphorus-containing, nitrogen-containing, carbonyl-containing silane from any unreacted components.

12. The compound of claim 1 that is:

wherein:
- R' is hydrogen or alkyl group having 1 to 3 carbon atoms or a mixture thereof between the three groups joined to the silicon;
- R is a methylene group and R° is a hydroxyl group or hydrogen and
- a and c are integers have values of 1 or zero and p is an integer from 1 to 3 and q is an integer from 1 to 6; and where when a and c are both zero, the compound is a salt with compound $I_{13}$ being the cation and the anion is selected from the group consisting of halides, sulfates, formates, acetates and phosphates.

13. Compound of claim 1, wherein the X trialkoxy organofunctional silane of moiety X is selected from the group consisting of: nitrogen-containing organofunctional silane, nitrogen-containing organosilane with at least one active hydrogen associated with the nitrogen and also having a carbon atom double bonded to an oxygen, epoxy-containing alkylalkoxy silane, anhydride-containing organofunctional silane, organofunctional silane with unsaturation in the organic moiety and an organosilane with haloalkyl or haloaryl moieties.

* * * * *

UNITED STATES PATENT AND TRADEMARK OFFICE
CERTIFICATE OF CORRECTION

PATENT NO. : 4,900,857
DATED : February 13, 1990
INVENTOR(S) : Michael W. Klett

It is certified that error appears in the above-identified patent and that said Letters Patent is hereby corrected as shown below:

Title page,
Item [57], ABSTRACT,
Line 1, change "silane" to read as -- silanes --.

Item [56], References Cited, U.S. PATENT DOCUMENTS, correct number "3,869,390" to read as -- 3,869,340 --.

Column 9,
Lines 40-44, insert the chemical equation between the words "carbonyl" and "or --CHOH radical" to read as iii) D ias a bivalent carbonyl $-\overset{\overset{\displaystyle O}{\|}}{C}-$ or -CHOH radical.

Column 9,
Line 31, change "yis" to read as -- y is --.

Column 10,
Line 50, correct "theeof" to read as -- thereof --.

Column 12,
Line 28, change "have" to read as -- having --.

Signed and Sealed this

Twenty-ninth Day of April, 2003

JAMES E. ROGAN
*Director of the United States Patent and Trademark Office*